United States Patent
McGuckin, Jr. et al.

(10) Patent No.: US 8,282,668 B2
(45) Date of Patent: **\*Oct. 9, 2012**

(54) VEIN FILTER

(75) Inventors: James F. McGuckin, Jr., Radnor, PA (US); Richard T. Briganti, Schwenksville, PA (US); Stephan A. DeFonzo, Wayne, PA (US); John H. Thinnes, Jr., Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 270 days.

This patent is subject to a terminal disclaimer.

(21) Appl. No.: 10/696,932

(22) Filed: Oct. 30, 2003

(65) Prior Publication Data

US 2005/0015111 A1 Jan. 20, 2005

Related U.S. Application Data

(63) Continuation-in-part of application No. 10/638,846, filed on Aug. 11, 2003, now abandoned, which is a continuation of application No. 09/883,819, filed on Jun. 18, 2001, now Pat. No. 6,623,506.

(60) Provisional application No. 60/466,807, filed on Apr. 30, 2003.

(51) Int. Cl.
*A61M 29/00* (2006.01)
*A61F 2/06* (2006.01)

(52) U.S. Cl. ........................................ 606/200; 606/198

(58) Field of Classification Search .................. 606/108, 606/110, 113, 194, 200, 157–159, 198
See application file for complete search history.

(56) References Cited

U.S. PATENT DOCUMENTS

| | | |
|---|---|---|
| 3,744,492 A | 7/1973 | Leibinsohn |
| 3,952,747 A | 4/1976 | Kimmell, Jr. |
| 4,425,908 A | 1/1984 | Simon |
| 4,494,531 A | 1/1985 | Gianturco |
| 4,512,338 A | 4/1985 | Balko et al. |
| 4,619,246 A | 10/1986 | Molgaard-Nielsen et al. |
| 4,688,553 A | 8/1987 | Metals |
| 4,727,873 A | 3/1988 | Mobin-Uddin |
| 4,781,177 A | 11/1988 | Lebigot |

(Continued)

FOREIGN PATENT DOCUMENTS

DE 3429850 2/1986

(Continued)

OTHER PUBLICATIONS

B. Braun Medical, Inc. Vena Tech™ Vena Cava Filters, Feb. 2000.

(Continued)

*Primary Examiner* — Kathleen Sonnett
*Assistant Examiner* — Sarah Webb
(74) *Attorney, Agent, or Firm* — Neil D. Gershon

(57) ABSTRACT

A vessel filter comprising a mounting section having first and second ends and a first and second filtering section. The filter is movable between a collapsed position for delivery to the vessel and an expanded position for placement within the vessel. In the expanded position a first end of the first filtering section converges to form a first converging region and a second end of the second filtering section converges to form a second converging region. The first converging region is positioned radially and axially inwardly of the first end of the mounting section and the second converging region is positioned radially and axially inwardly of the second end of the mounting section.

13 Claims, 14 Drawing Sheets

U.S. PATENT DOCUMENTS

| | | | |
|---|---|---|---|
| 4,793,348 | A | 12/1988 | Palmaz |
| 4,817,600 | A | 4/1989 | Herms et al. |
| 4,832,055 | A | 5/1989 | Palestrant |
| 4,957,501 | A | 9/1990 | Lahille et al. |
| 4,990,156 | A | 2/1991 | Lefebvre |
| 4,994,069 | A | 2/1991 | Ritchart et al. |
| 5,059,205 | A | 10/1991 | El-Nounou et al. |
| 5,133,733 | A | 7/1992 | Rasmussen et al. |
| 5,152,777 | A | 10/1992 | Goldberg et al. |
| 5,234,458 | A | 8/1993 | Metais |
| 5,300,086 | A | 4/1994 | Gory et al. |
| 5,324,304 | A | 6/1994 | Rasmussen |
| 5,344,427 | A | 9/1994 | Cottenceau et al. |
| 5,350,398 | A | 9/1994 | Pavcnik et al. |
| 5,370,657 | A | 12/1994 | Irie |
| 5,375,612 | A | 12/1994 | Cottenceau et al. |
| 5,382,261 | A | 1/1995 | Palmaz |
| 5,383,887 | A | 1/1995 | Nadal |
| 5,405,377 | A | 4/1995 | Cragg |
| 5,531,788 | A | 7/1996 | Dibie et al. |
| 5,591,197 | A | 1/1997 | Orth et al. |
| 5,601,595 | A | 2/1997 | Smith |
| 5,626,605 | A | 5/1997 | Irie et al. |
| 5,634,942 | A | 6/1997 | Chevillon et al. |
| 5,681,347 | A | 10/1997 | Catheart et al. |
| 5,683,411 | A | 11/1997 | Kavteladze et al. |
| 5,690,671 | A | 11/1997 | McGurk et al. |
| 5,709,704 | A | 1/1998 | Nott et al. |
| 5,725,552 | A | 3/1998 | Kotula et al. |
| 5,733,294 | A | 3/1998 | Forber et al. |
| 5,733,329 | A | 3/1998 | Wallace et al. |
| 5,746,767 | A | 5/1998 | Smith |
| 5,755,779 | A | 5/1998 | Horiguchi |
| 5,755,790 | A | 5/1998 | Chevillon et al. |
| 5,776,162 | A | 7/1998 | Kleshinski |
| 5,795,322 | A | 8/1998 | Boudewijn |
| 5,810,874 | A | 9/1998 | Lefebvre |
| 5,836,968 | A | 11/1998 | Simon et al. |
| 5,853,420 | A | 12/1998 | Chevillon et al. |
| 5,893,869 | A | 4/1999 | Barnhart et al. |
| 5,895,398 | A | 4/1999 | Wensel et al. |
| 5,895,410 | A | 4/1999 | Forber et al. |
| 5,911,717 | A | 6/1999 | Jacobsen et al. |
| 5,968,071 | A | 10/1999 | Chevillon et al. |
| 5,976,172 | A | 11/1999 | Homsma et al. |
| 5,984,947 | A | 11/1999 | Smith |
| 6,007,558 | A | 12/1999 | Ravenscroft et al. |
| 6,013,093 | A | 1/2000 | Nott et al. |
| 6,042,598 | A | 3/2000 | Tsugita et al. |
| 6,059,825 | A | 5/2000 | Hobbs et al. |
| 6,063,113 | A | 5/2000 | Kavteladze et al. |
| 6,066,158 | A | 5/2000 | Engelson et al. |
| 6,080,178 | A | 6/2000 | Meglin |
| 6,093,196 | A | 7/2000 | Okada |
| 6,093,199 | A | 7/2000 | Brown et al. |
| 6,096,052 | A | 8/2000 | Callister et al. |
| 6,099,549 | A | 8/2000 | Bosma et al. |
| 6,117,154 | A | 9/2000 | Barbut et al. |
| 6,123,715 | A | 9/2000 | Amplatz |
| 6,126,673 | A | 10/2000 | Kim et al. |
| 6,146,604 | A | 11/2000 | Kim et al. |
| 6,152,946 | A | 11/2000 | Broome et al. |
| 6,165,179 | A | 12/2000 | Cathcart et al. |
| 6,165,198 | A | 12/2000 | McGurk et al. |
| 6,168,579 | B1 | 1/2001 | Tsugita |
| 6,168,603 | B1 | 1/2001 | Leslie et al. |
| 6,171,327 | B1 | 1/2001 | Daniel et al. |
| 6,171,328 | B1 | 1/2001 | Addis |
| 6,179,851 | B1 | 1/2001 | Barbut et al. |
| 6,179,859 | B1 | 1/2001 | Bates et al. |
| 6,187,025 | B1 | 2/2001 | Machek |
| 6,193,739 | B1 | 2/2001 | Chevillon et al. |
| 6,214,025 | B1 | 4/2001 | Thistle et al. |
| 6,217,600 | B1 | 4/2001 | DiMatteo |
| 6,231,581 | B1 | 5/2001 | Shank et al. |
| 6,231,589 | B1 | 5/2001 | Wessman et al. |
| 6,235,044 | B1 | 5/2001 | Root et al. |
| 6,235,045 | B1 | 5/2001 | Barbut et al. |
| 6,241,746 | B1 * | 6/2001 | Bosma et al. ................ 606/200 |
| 6,245,012 | B1 | 6/2001 | Kleshinski |
| 6,251,122 | B1 | 6/2001 | Tsukernik |
| 6,258,026 | B1 | 7/2001 | Ravenscroft et al. |
| 6,267,776 | B1 | 7/2001 | O'Connell |
| 6,273,901 | B1 | 8/2001 | Whitcher et al. |
| 6,280,451 | B1 | 8/2001 | Bates et al. |
| 6,280,457 | B1 | 8/2001 | Wallace et al. |
| 6,290,721 | B1 | 9/2001 | Heath |
| 6,331,184 | B1 | 12/2001 | Abrams |
| 6,342,062 | B1 | 1/2002 | Suon et al. |
| 6,342,063 | B1 | 1/2002 | Devries et al. |
| 6,344,041 | B1 | 2/2002 | Kupiecki et al. |
| 6,355,051 | B1 | 3/2002 | Sisskind et al. |
| 6,402,771 | B1 | 6/2002 | Palmer et al. |
| 6,436,120 | B1 | 8/2002 | Meglin |
| 6,436,121 | B1 | 8/2002 | Blom |
| 6,443,971 | B1 | 9/2002 | Boylan et al. |
| 6,443,972 | B1 | 9/2002 | Bosma et al. |
| 6,447,530 | B1 | 9/2002 | Ostrovsky et al. |
| 6,447,531 | B1 | 9/2002 | Amplatz |
| 6,458,139 | B1 | 10/2002 | Palmer et al. |
| 6,468,290 | B1 | 10/2002 | Weldon et al. |
| 6,482,222 | B1 | 11/2002 | Bruckheimer et al. |
| 6,506,205 | B2 | 1/2003 | Goldberg et al. |
| 6,517,559 | B1 | 2/2003 | O'Connell |
| 6,527,962 | B1 | 3/2003 | Nadal |
| 6,537,294 | B1 | 3/2003 | Boyle et al. |
| 6,540,767 | B1 | 4/2003 | Walak et al. |
| 6,551,342 | B1 | 4/2003 | Shen et al. |
| 6,562,058 | B2 | 5/2003 | Seguin et al. |
| 6,589,265 | B1 * | 7/2003 | Palmer et al. ................ 606/200 |
| 6,605,102 | B1 | 8/2003 | Mazzocchi et al. |
| 6,652,558 | B2 | 11/2003 | Patel et al. |
| 6,660,021 | B1 | 12/2003 | Palmer et al. |
| 6,695,878 | B2 | 2/2004 | McGuckin et al. |
| 6,783,538 | B2 | 8/2004 | McGuckin et al. |
| 6,793,665 | B2 | 9/2004 | McGuckin et al. |
| 6,890,340 | B2 | 5/2005 | Duane |
| 6,932,831 | B2 | 8/2005 | Forber |
| 6,958,074 | B2 | 10/2005 | Russell |
| 6,972,025 | B2 | 12/2005 | WasDyke |
| 6,989,021 | B2 | 1/2006 | Bosma et al. |
| 6,994,092 | B2 * | 2/2006 | van der Burg et al. ........ 606/200 |
| 7,037,321 | B2 | 5/2006 | Sachdeva et al. |
| 7,097,651 | B2 * | 8/2006 | Harrison et al. ............. 606/200 |
| 2002/0058911 | A1 | 5/2002 | Gilson et al. |
| 2002/0116024 | A1 | 8/2002 | Goldberg et al. |
| 2002/0193827 | A1 | 12/2002 | McGuckin et al. |
| 2003/0130680 | A1 | 7/2003 | Russell |
| 2003/0195555 | A1 * | 10/2003 | Khairkhahan et al. ........ 606/200 |
| 2003/0208227 | A1 | 11/2003 | Thomas |
| 2003/0208253 | A1 | 11/2003 | Beyer et al. |
| 2004/0186510 | A1 | 9/2004 | Weaver |
| 2004/0230220 | A1 | 11/2004 | Osborne |
| 2005/0004596 | A1 | 1/2005 | McGuckin et al. |
| 2005/0043757 | A1 | 2/2005 | Arad et al. |

FOREIGN PATENT DOCUMENTS

| | | |
|---|---|---|
| WO | WO 9312723 | 7/1993 |
| WO | WO 95 09567 | 4/1995 |
| WO | WO 99 25252 | 5/1999 |
| WO | WO 01 45590 | 6/2001 |
| WO | WO 01 62184 | 8/2001 |
| WO | WO 01 72239 | 10/2001 |
| WO | 0211812 | 2/2002 |
| WO | WO 2004 049973 | 6/2004 |

OTHER PUBLICATIONS

Gianturco-Roehm, Bird's Nest® Vena Cava Filter.

Cordis Corporation, TrapEase™ Permanent Vena Cava Filter, "A Small, Easy and Verstaile System for Optimal Pulmonary Emboli Prevention", 2000 (4 pages).

* cited by examiner

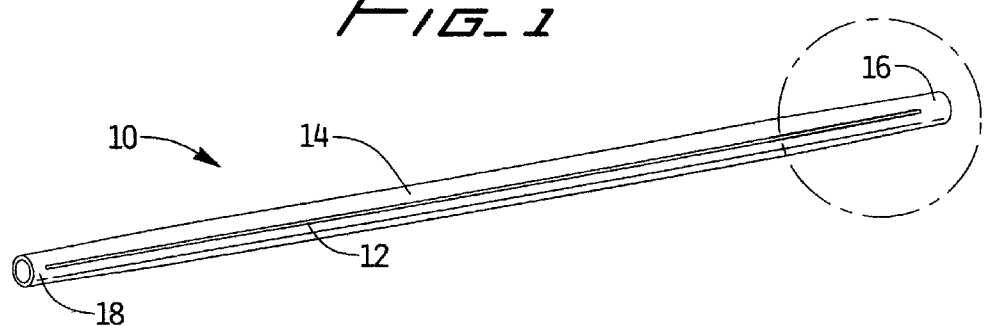
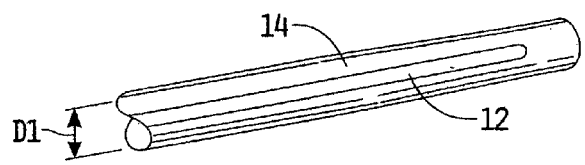
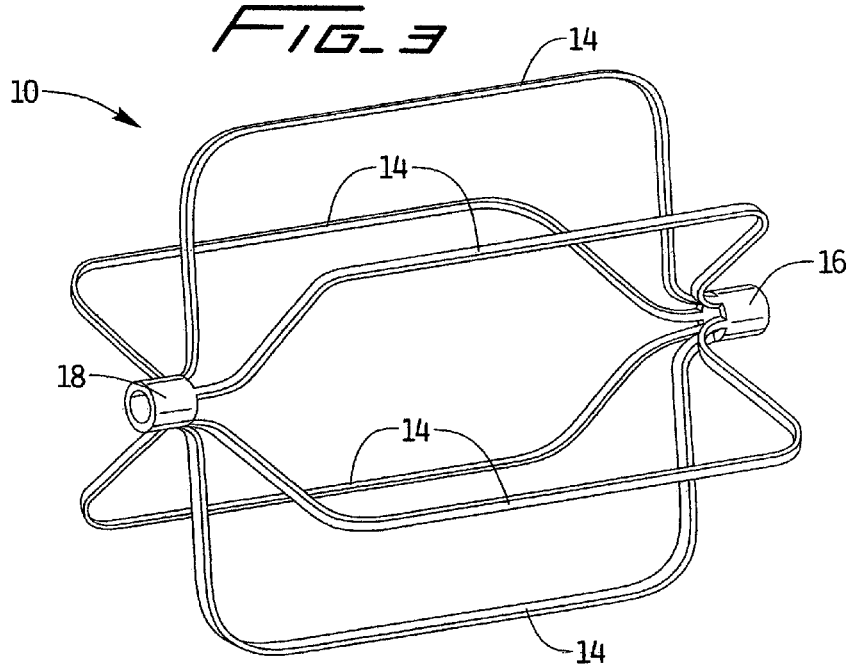

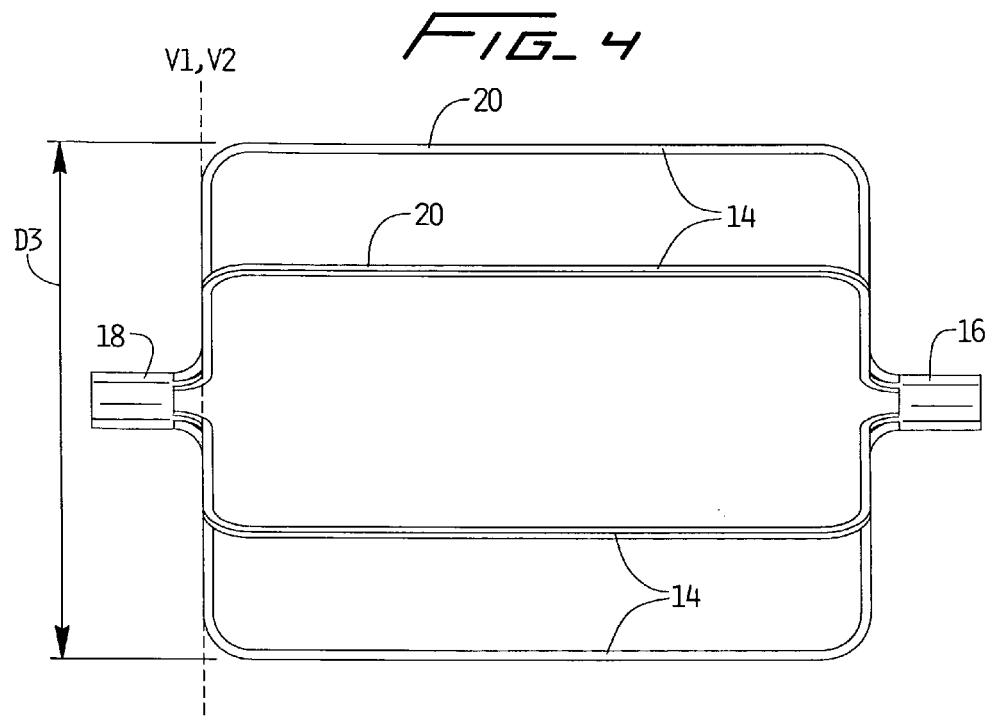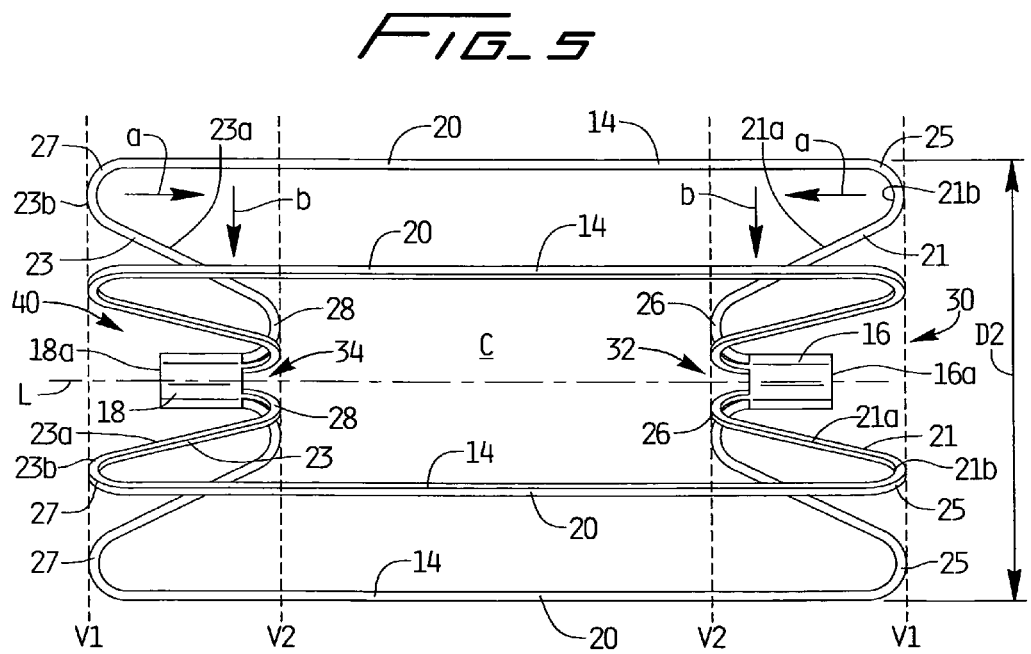

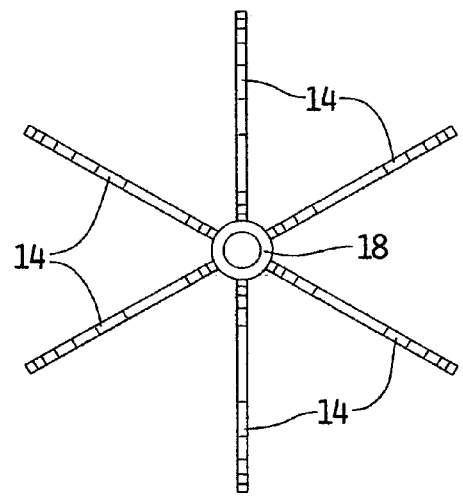
FIG_6
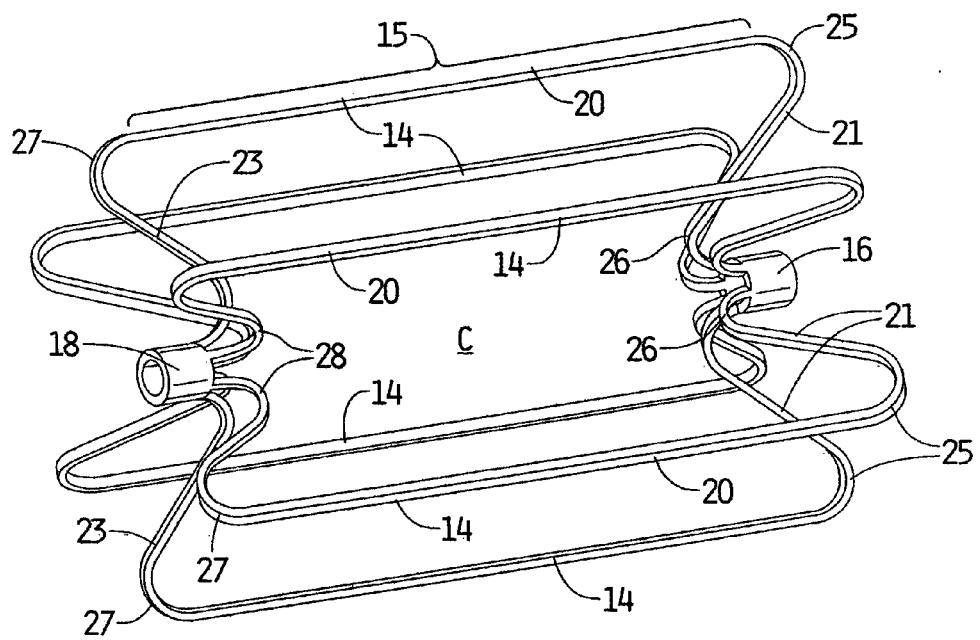
FIG_7

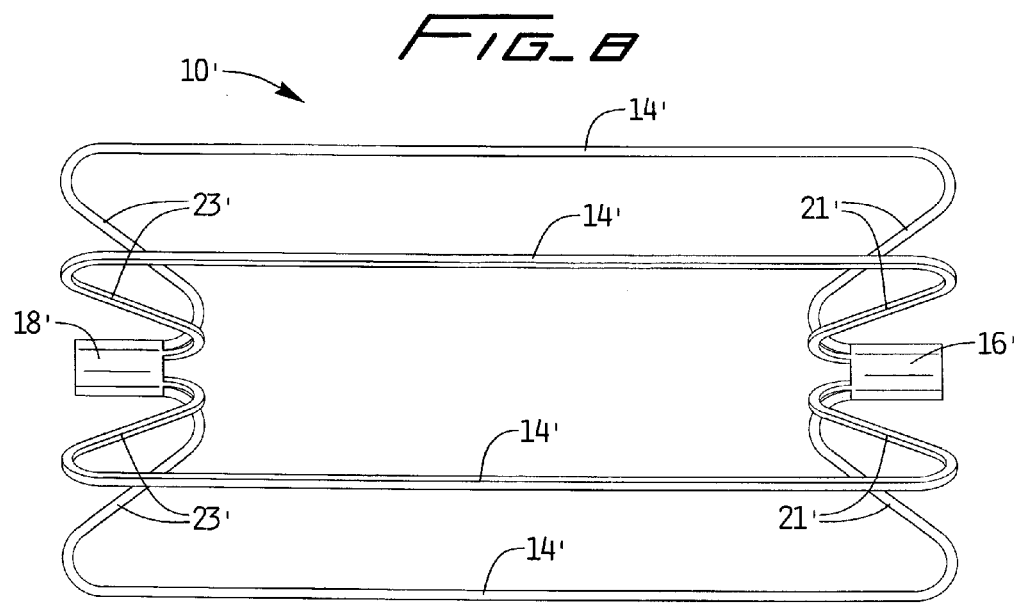
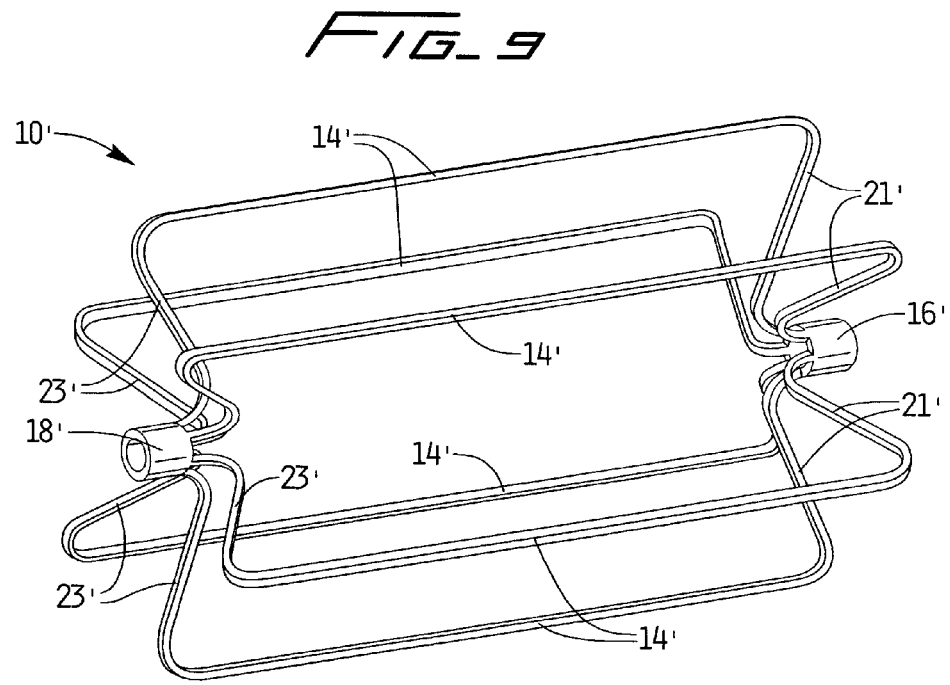

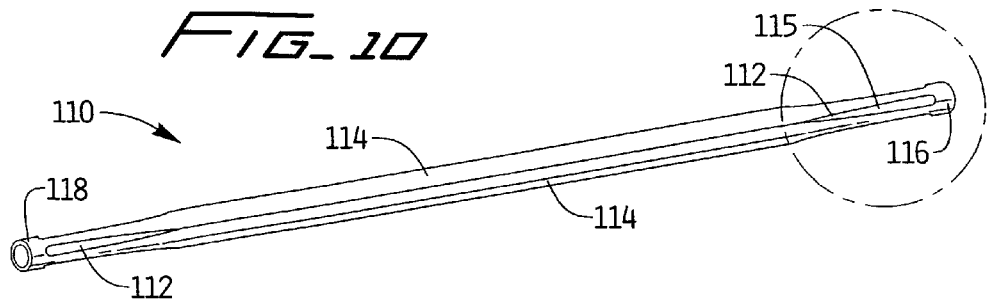
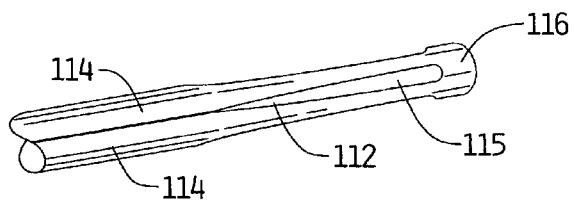
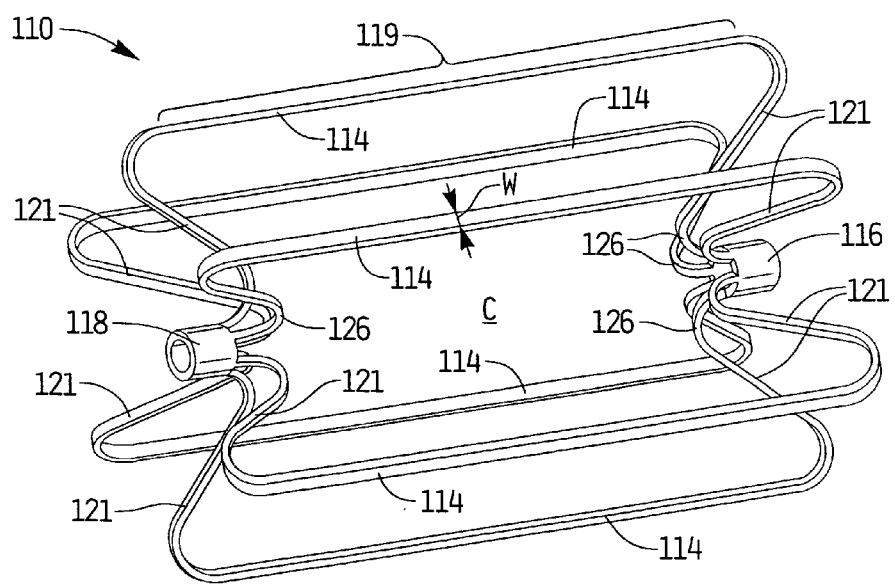

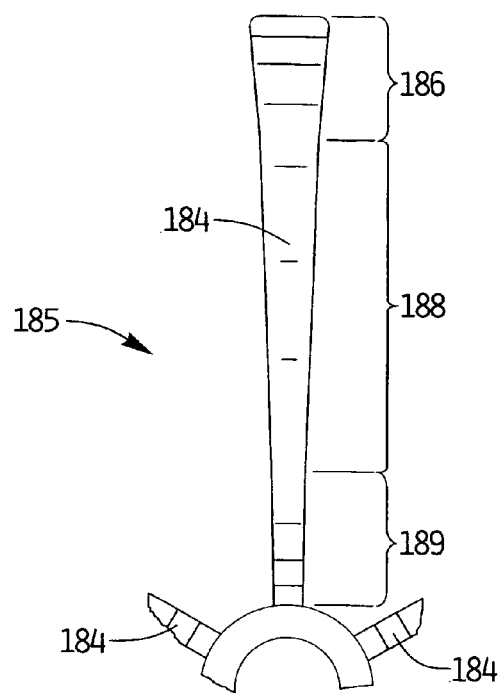
FIG_13
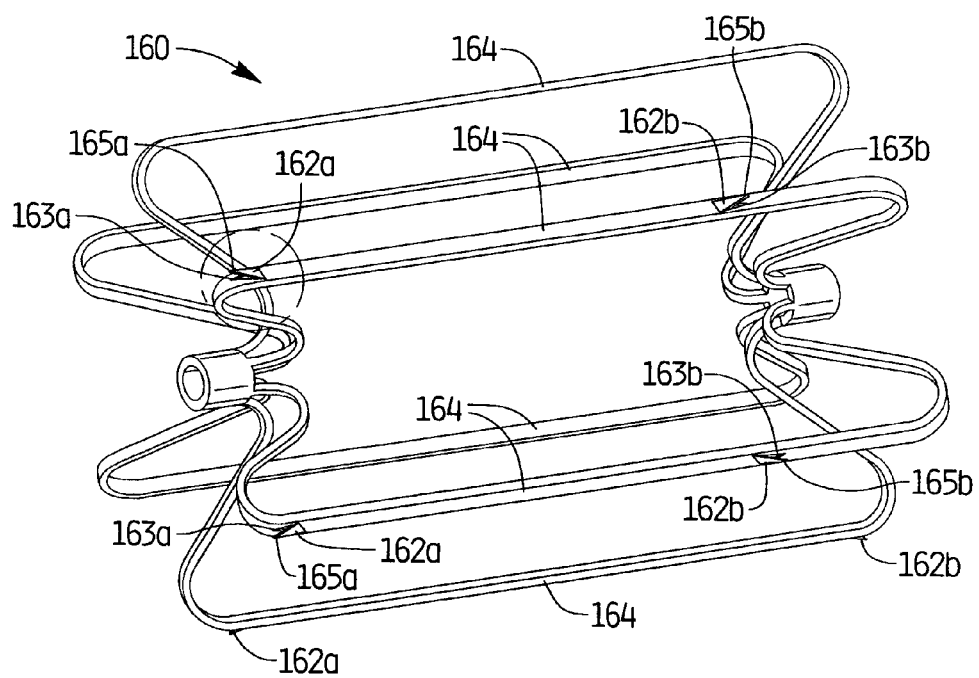
FIG_16A

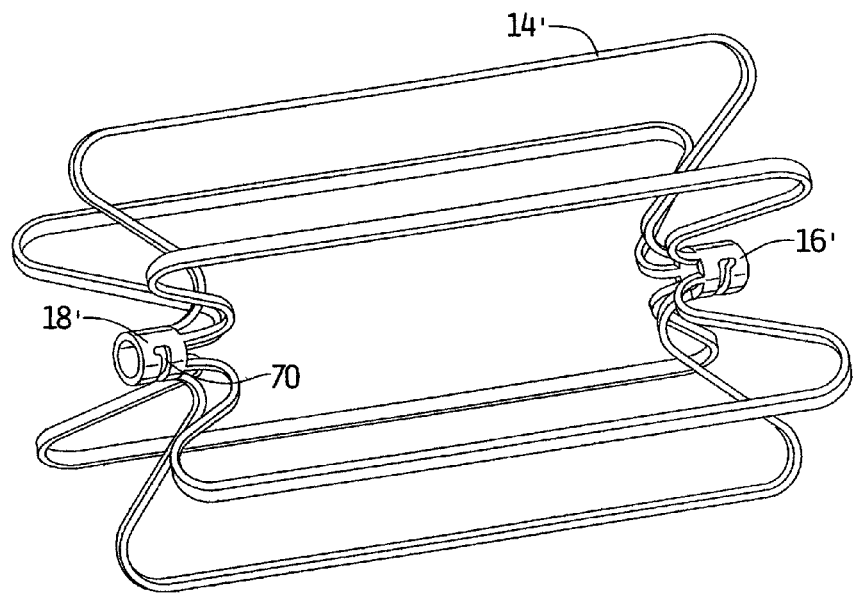
FIG_14A
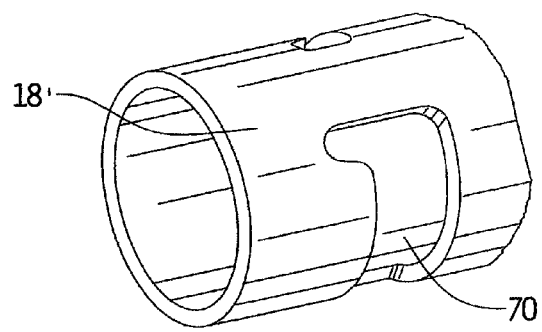
FIG_14B
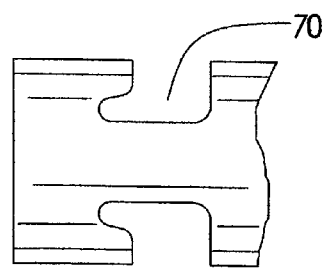
FIG_14C

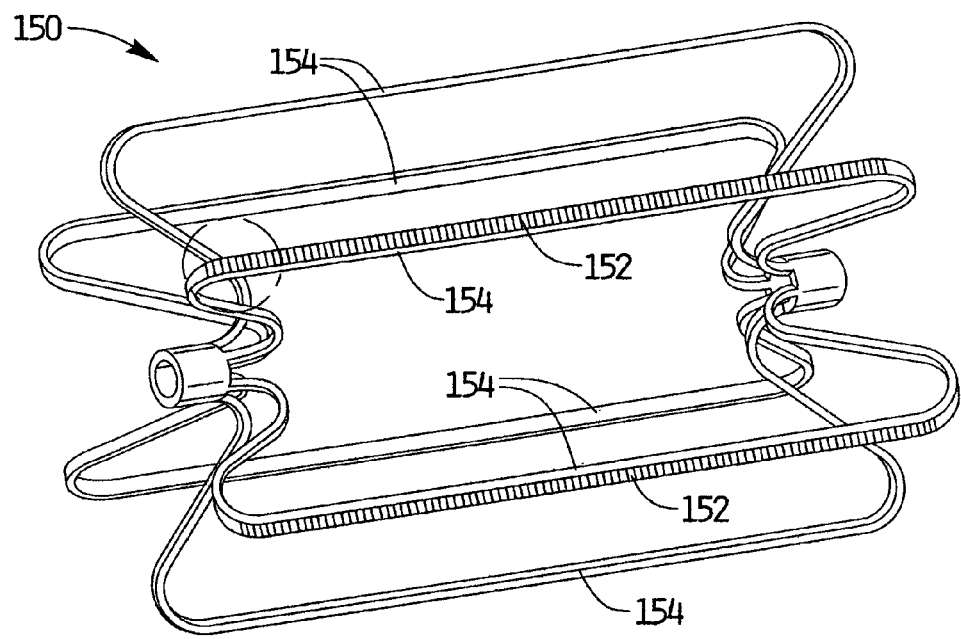
FIG_15A
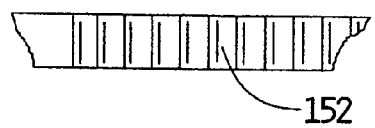
FIG_15B
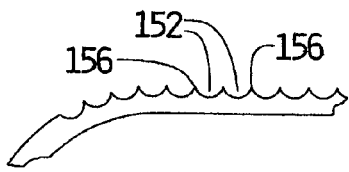
FIG_15C

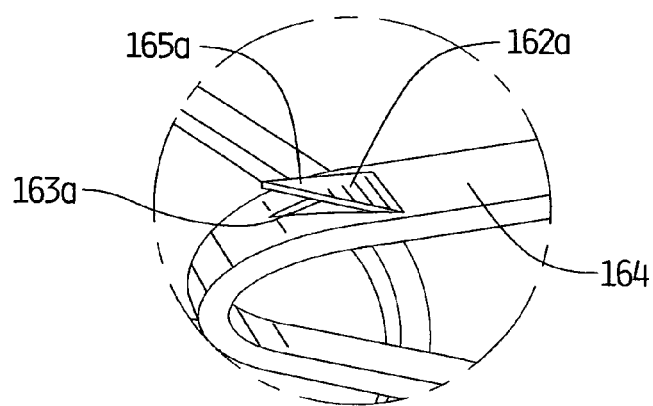
FIG_16B
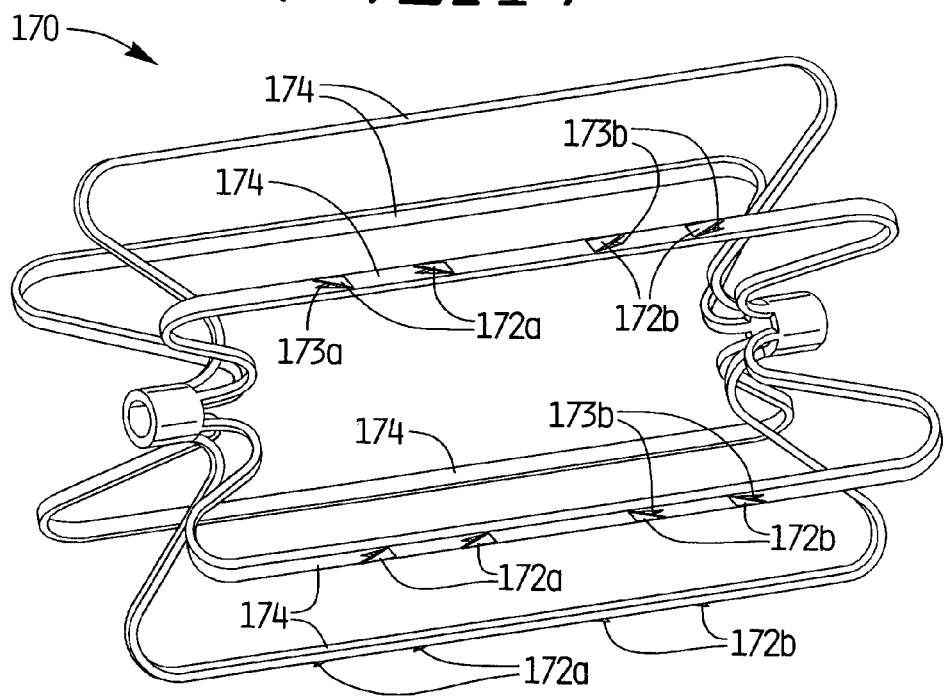
FIG_17

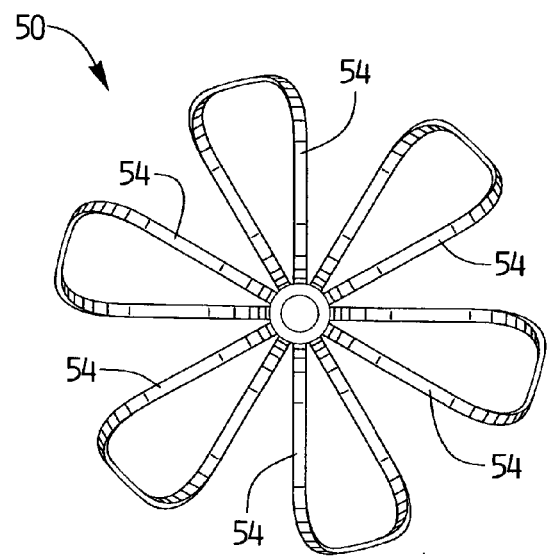
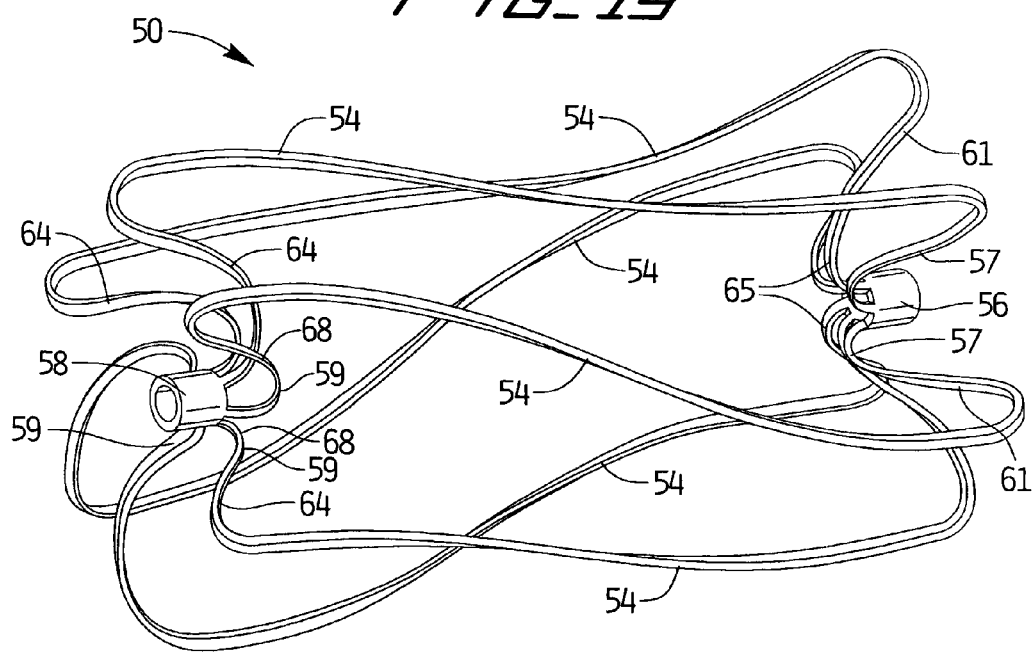

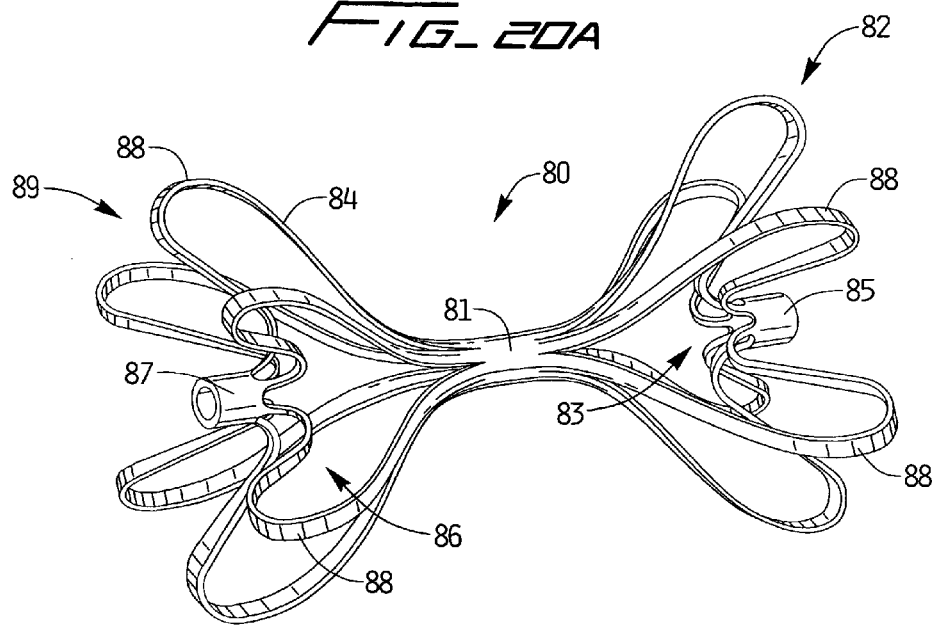
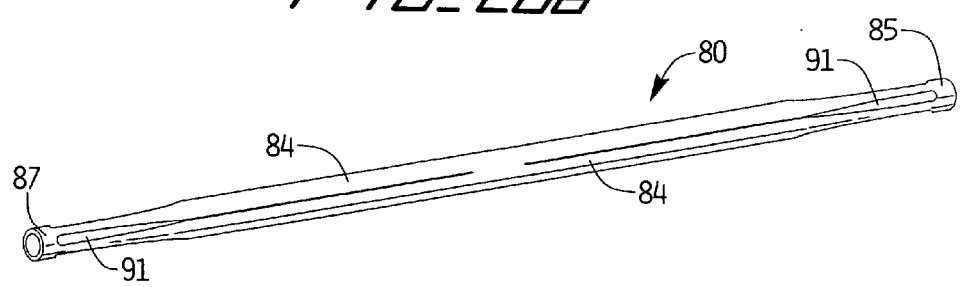

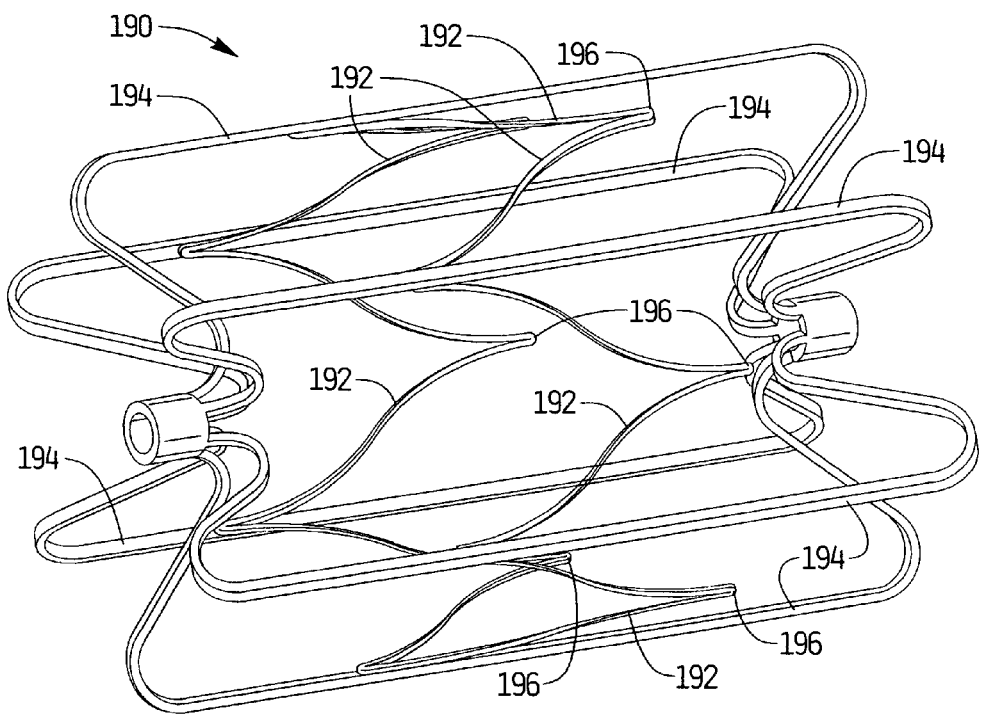
FIG_21A
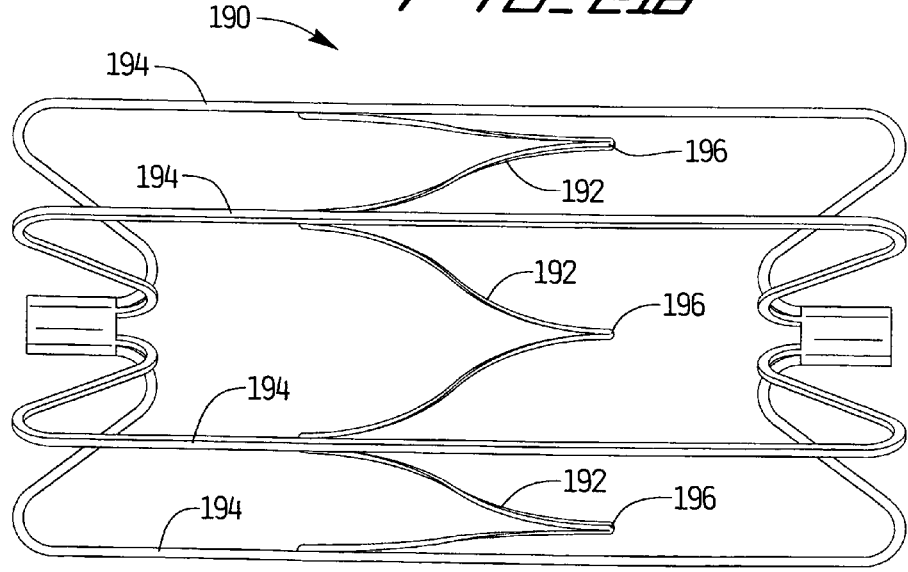
FIG_21B

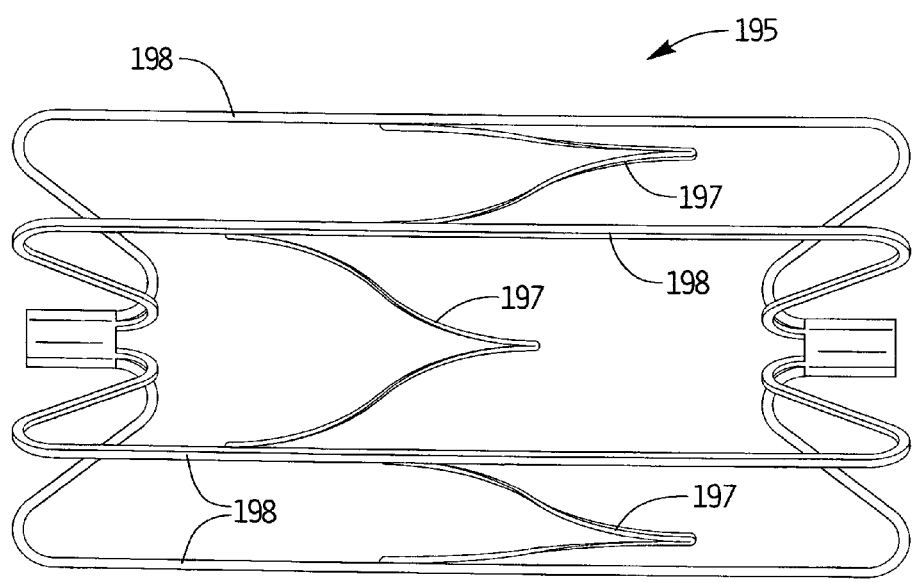

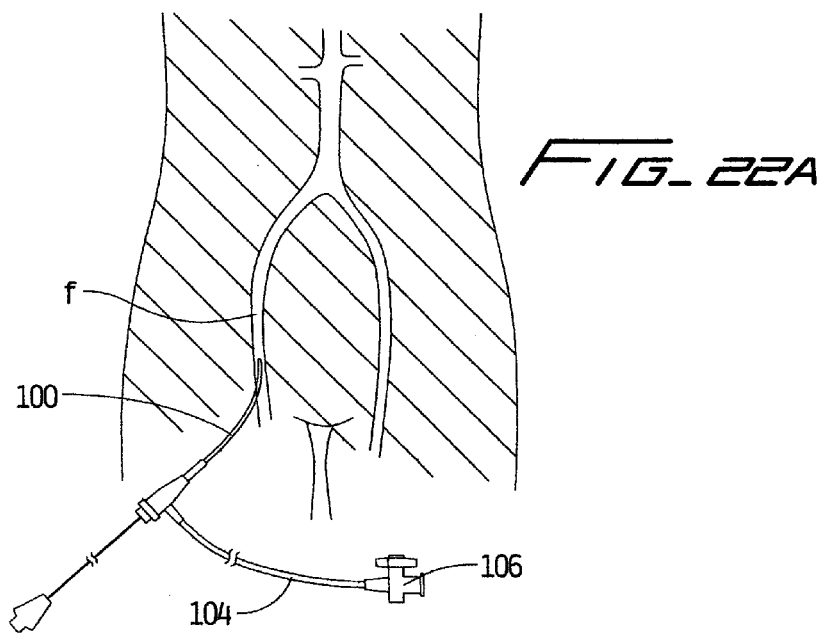
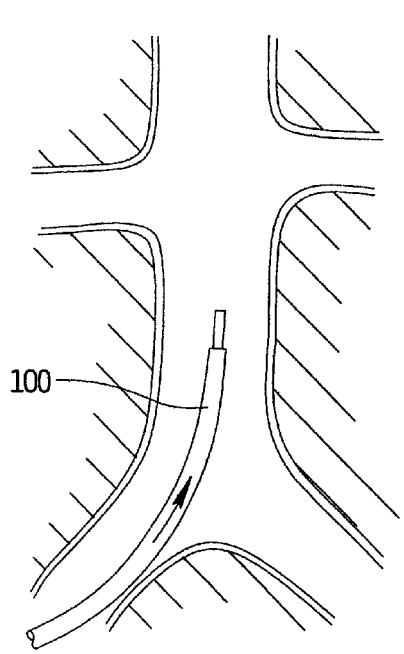
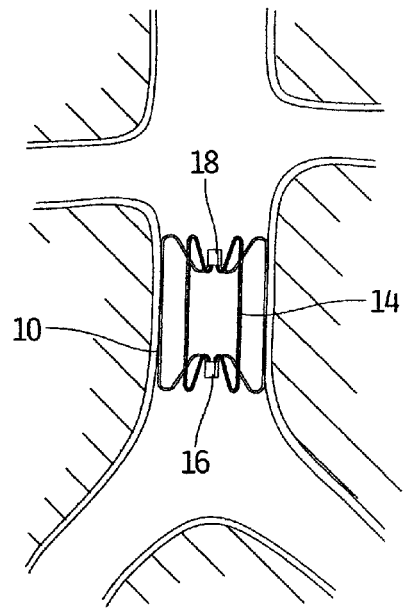

VEIN FILTER

This application claims priority from provisional patent application 60/466,807, filed Apr. 30, 2003 and is a continuation-in-part of application Ser. No. 10/638,846 filed Aug. 11, 2003 now abandoned which is a continuation of Ser. No. 09/883,819, filed Jun. 18, 2001, now U.S. Pat. No. 6,623,506, the entire contents of each of these applications are incorporated herein by reference.

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

It would be advantageous to provide a vein filter that satisfies the foregoing parameters. Namely, such vein filter would advantageously have sufficient anchoring force to retain the filter within the vessel while providing atraumatic contact with the vessel wall, would have a minimized insertion (collapsed) profile to facilitate delivery through the vascular system to the surgical site, and would enable migration of the captured blood clots to the center of the vessel. Moreover, it would also be advantageous to provide a filter that could simplify insertion through the femoral or the right jugular vein or arm into the inferior vena cava.

Additionally, the need for a vein filter in many patients is temporary. In these instances it would be advantageous to provide a vein filter that satisfies the foregoing factors and in addition could be readily removed from the patient. It would further be advantageous if the filter could be removed minimally invasively, e.g. intravascularly, and further advantageous if the filter could be removed from the inferior vena cava in either direction, e.g. through femoral or internal jugular vein access.

SUMMARY

The present invention overcomes the problems and deficiencies of the prior art. The present invention provides a vessel filter comprising a mounting section having first and second ends and first and second filtering sections. The filter is movable between a collapsed position for delivery to the vessel and an expanded position for placement within the vessel. In the expanded position a first end of the first filtering section converges to form a first converging region and a second end of the second filtering section converges to form a second converging region, wherein the first converging region is positioned radially and axially inwardly of the first end of the mounting section and the second converging region is positioned radially and axially inwardly of the second end of the mounting section.

The filter is preferably composed of a single tube of shape memory material having cutouts therein forming a plurality of elongated struts. Preferably, portions of the filter connecting the first and second ends of the mounting sections to the respective converging region angle radially inwardly and toward a center of the filter to direct particles toward the center.

In one embodiment, the elongated struts include roughened surfaces to engage the vessel wall to increase retention. In another embodiment, a plurality of vessel engaging barbs extend from the longitudinal struts to engage the vessel wall to increase retention. In one embodiment, the filter has a converging region at a central region of the filter. In this embodiment the first and second converging regions and the converging region at the central region may each include a tubular region.

The present invention also provides an apparatus comprising a vessel filter having a tubular member having a plurality of cutouts formed therein forming a series of spaced apart struts and movable between a first insertion configuration and a second deployed configuration. In the second configuration the struts extend substantially longitudinally and form a mounting section extending from a first end to a second end, wherein the struts further extend from the first end and from the second end radially inwardly towards a center of the filter to form first and second filtering sections such that the filtering sections are each positioned nearer a center of the filter than the first and second ends of the mounting section.

Preferably, the first filtering section and the second filtering section each have a converging region. The filter is preferably composed of a shape memory tubular material. The filter can include a plurality of vessel engaging members. The width of the strut of the filter can vary along its length.

In one embodiment of the foregoing filters, the end portions of at least one of the elongated struts are axially offset or out of phase.

In one embodiment of the foregoing filters, a rib connects adjacent struts.

The present invention also provides a method of implanting a vessel filter in a patient's body comprising the steps of:

providing a vessel filter having a mounting section and first and second filtering sections each terminating in a converging end region;

providing a tubular delivery member containing the vessel filter in a collapsed configuration having a first diameter;

inserting the vessel filter in the collapsed configuration adjacent a surgical site; and deploying the vessel filter from the delivery member so the vessel filter moves to a placement configuration having a diameter larger than the first diameter and the converging end regions of the filtering sections are closer to a center of the filter than end portions of the mounting section.

Preferably, the vessel filter is composed of shape memory material and movement of the vessel filter to the placement configuration moves the vessel filter towards a memorized configuration. The method may further include the step of removing the implanted vessel filter from the patient's body.

BRIEF DESCRIPTION OF THE DRAWINGS

Preferred embodiment(s) of the present disclosure are described herein with reference to the drawings wherein:

FIG. 1 is a perspective view of the vein filter of the present invention in the collapsed configuration;

FIG. 2 is a close up view of one end of the vein filter of FIG. 1;

FIG. 3 is a perspective view of the vein filter in the transitional expanded configuration wherein the converging filter portions and the mounting section are in substantial axial alignment;

FIG. 4 is a side view of the filter in the transitional expanded configuration of FIG. 3;

FIG. 5 is a side view of the vein filter in the expanded placement configuration wherein the converging filter portions are spaced axially inwardly from the ends of the mounting sections;

FIG. 6 is a front view of the vein filter in the expanded placement configuration of FIG. 5;

FIG. 7 is a perspective view of the vein filter in the placement configuration of FIG. 5;

FIGS. 8 and 9 are side and perspective views, respectively, of an alternate embodiment of the vein filter of the present invention shown in the expanded placement configuration;

FIGS. 10-12 illustrate another alternate embodiment of the vein filter having struts with varying widths wherein FIG. 10 is a perspective view of the vein filter in the collapsed configuration, FIG. 11 is a close up view of one end of the vein filter in the collapsed configuration, and FIG. 12 is a perspective view of the vein filter in the expanded placement configuration;

FIG. 13 is an enlarged partial front view of another alternate embodiment of the struts having a varying width;

FIG. 14A is a perspective view of an alternate embodiment of the filter having a cutout to receive a retrieval snare, the filter shown in the expanded configuration;

FIGS. 14B and 14C are close up perspective and side views, respectively of an end of the filter of FIG. 14A;

FIG. 15A is a perspective view of the vein filter in an expanded configuration showing a first embodiment of anchoring elements for anchoring the filter;

FIGS. 15B and 15C are top and side views, respectively, of the anchoring elements of FIG. 15A;

FIG. 16A is a perspective view showing an alternate embodiment of anchoring elements for anchoring the filter, the filter shown in the expanded configuration;

FIG. 16B is a close up view of an anchoring element of FIG. 16A;

FIG. 17 is a view similar to FIG. 16A except showing another alternate embodiment of anchoring elements;

FIG. 18 is a perspective view of another alternate embodiment of the vein filter of the present invention with opposing strut end portions out of phase and shown in the expanded placement configuration;

FIG. 19 is a front view of the vein filter of FIG. 18A;

FIG. 20A is a perspective view of another alternate embodiment of the vein filter of the present invention with the intermediate region converging and shown in the expanded placement configuration;

FIG. 20B is a perspective view of the vein filter of FIG. 20A in the collapsed configuration;

FIGS. 21A and 21B are perspective and side views of another alternate embodiment of the vein filter having stabilizing ribs extending between the struts;

FIG. 21C is a side view of an alternate embodiment of the vein filter of FIG. 21A having staggered stabilizing ribs;

FIGS. 22A, 22B and 22C illustrate delivery and placement of the vessel filter of FIG. 1 in the inferior vena cava wherein FIG. 22A illustrates initial insertion of the delivery sheath through the femoral vein, FIG. 22B illustrates the delivery sheath being advanced toward the inferior vena cava just below (upstream) the juncture of the renal arteries; and FIG. 22C illustrates the delivery sheath fully withdrawn to place the filter in the expanded placement configuration in the inferior vena cava.

DETAILED DESCRIPTION OF PREFERRED EMBODIMENTS

Turning now to the drawings, wherein like reference numerals identify similar or like components throughout the several views, the vein filter of the present invention is described for placement within the inferior vena cava to capture blood clots or other particles which could otherwise pass to the lungs. The filter is movable from a low profile collapsed configuration to facilitate insertion through the delivery sheath to a larger expanded placement configuration to enable atraumatic engagement with the vessel walls to secure (mount) the filter within the inferior vena cava. The filter has a mounting section forming the outermost transverse boundary of the filter and two filtering portions (sections) at the opposing ends of the filter. As described in more detail below, each filtering portion is spaced both radially and axially inwardly from an end of the mounting section and has a converging region.

Turning now to details of the filter of the present invention and with initial reference to FIGS. 1 and 2, the filter is designated generally by reference numeral 10 and is shown in a collapsed configuration for delivery. Filter 10 is preferably formed from a single tube. In a preferred embodiment, the filter 10 is composed of shape memory material, such as Nitinol, a nickel titanium alloy, however, other materials such as stainless steel are also contemplated. A plurality of cutouts 12 are formed in the filter 10, preferably by laser cutting although other techniques are contemplated. In the illustrated embodiment, six elongated cutouts are formed of substantially uniform width creating six elongated strips or struts 14 of substantially uniform width separated by the cutouts and terminating in tubular portions 16, 18 at the ends.

The collapsed configuration of filter 10 reduces the overall profile to facilitate delivery to the site. The diameter of filter 10 in the collapsed configuration is represented by reference D1 and preferably is about 2 mm, and more preferably about 1.7 mm. Other dimensions are also contemplated.

FIGS. 5 and 7 illustrate the expanded placement configuration of the filter 10. In this configuration, the filter has expanded to a diameter D2. Diameter D2 preferably ranges from about 18 mm to about 32 mm, depending on the internal diameter of the vessel wall as will be explained in more detail below. Other dimensions are also contemplated. The elongated struts 14 extend substantially parallel to the longitudinal axis L of filter 10 in the mounting section (portion) 15 and are spaced apart as shown. In the illustrated embodiment, when expanded, the six struts 14 are shown spaced approximately 60 degrees apart. It is also contemplated that a fewer or greater number of struts could be provided and spacing other than 60 degrees be provided. The length of the struts is preferably greater than the diameter of the filter 10 to provide additional longitudinal stability and decrease the likelihood of the filter rolling out of position. In a preferred embodiment the longitudinal component of the struts 14, i.e. the component of the strut extending substantially parallel to the longitudinal axis of the filter and forming the mounting section 15, is about 3.6 cm in length, although other dimensions are also contemplated.

In the expanded placement configuration, each longitudinal strut 14 has an elongated (longitudinal component) outer surface 20 for engagement with the vessel wall to retain the filter 10 in position in the vessel. The outer surface 20 could be roughened to enhance engagement. Alternatively, a plurality of atraumatic tabs, barbs or other penetrating members can extend from the outer surface 20 of the struts 14 to engage the vessel wall to retain the filter. FIGS. 15, 16 and 17 show examples of such retention features. In FIGS. 15A-15C, filter 150 has a series of hemispherical cutouts 152 formed along the length of the struts 154 forming pointed edges 156 to engage the vessel wall. Although shown along the length of the strut 154, the cutouts 152 can alternatively be formed only along a portion of the length. The cutouts can also be formed on fewer than all the struts 154.

In the embodiment of FIGS. 16A-16B, the filter 160 has anchoring elements 162*a*, 162*b* formed by cutouts 163*a*, 163*b* at the ends of the mounting section of the struts 164. Anchoring elements 162*a* have pointed ends 165a facing in a first direction towards the first end of the filter and anchoring elements 162*b* have pointed ends 165b facing in a second direction towards the second end of the filter. In the collapsed configuration the anchoring elements 162*a*, 162*b* and their pointed ends 165*a*, 165*b* are aligned with the struts 164, substantially parallel with the longitudinal axis of the filter to maintain a reduced profile. When the filter 160 moves to the expanded configuration, the pointed ends 165*a*, 165*b* face outwardly as shown in FIG. 16A. Anchoring elements 162*a*, 162*b* are preferably placed in the regions of the strut adjacent the curve or bend, as in elements 162*a*, although other locations are also contemplated such as anchoring element 162*b* spaced from the curve or bend. In a preferred embodiment, elements 162*b* would also be placed adjacent the curve or bend in the struts 14.

In the embodiment of FIG. 17, anchoring elements 172*a*, 172*b* of filter 170 are formed along the length of the struts 174 positioned axially inwardly of the opposing end of the mounting portion. That is, they are axially inward of the regions of the struts where the bends are formed. Anchoring elements 172*a*, 172*b* are similar to elements 162*a*, 162*b* in that they have pointed ends facing in opposite directions as shown and are formed by cutouts 173*a*, 173*b* in the struts 174. They are also aligned with the struts 174 in the collapsed configuration in the same manner as anchoring elements 162*a*, 162*b*. In the view of FIGS. 16A and 17, anchoring elements 162*a*, 162*b* and 172*a*, 172*b* can be seen on only three of the struts, it being appreciated that they can be formed on all or any number of struts. Also, although six struts are shown, as with the other embodiments herein, a different number of struts is also contemplated.

Referring back to FIGS. 5 and 7, the filtering sections (portions) of filter 10 are designated generally by reference numerals 30 and 40. Each filtering section 30, 40 extends from the mounting section 20 and is formed by the angled component of the struts 14. Filtering section 30 converges at region 32 into tubular portion 16 while filtering section 40 converges at region 34 into tubular portion 18. Each longitudinal strut 14 extends substantially parallel to the longitudinal axis of the filter in the mounting section 15 as described above. The ends 25, 27 of each longitudinal strut 14 bend inwardly towards the center C of the filter 10 forming respective angled strut portions 21, 23. These angled struts 21, 23 thereby each extend both radially inwardly and axially inwardly toward the respective filtering section 30, 40. The angled struts 21, 23 have a linear portions 21*a*, 23*a* which extend from respective curved regions 21*b*, 23*b* and transitions to respective curved portions 26, 28, curved in an outward direction to transition to the respective tubular portions 16, 18 of the filtering section 30, 40. For clarity, not all of these sections of each strut 14 are labeled in the drawing, it being understood that the non-labeled struts have the same configurations.

It should be understood that the longitudinal struts 14 bend as they move from their collapsed position to their expanded placement configuration. Their designations of longitudinal, angled, curved, etc refer to the same integral strut and are divided into such regions for ease of understanding. Therefore, stated another away, the filter 10 can be viewed as having a filtering section 30 at a proximal end and a filtering section 40 at a distal end with tubular portions 16, 18 at the proximal and distal ends, respectively. As viewed, each of the struts 14 emerges from the tubular portion 16 in curved region 26 which initially extends inwardly toward the center C of the filter 10 and then curves outwardly away from the center C to transition to angled portion 21 which extends outwardly away from the center. The angled portions 21 bend inwardly at region 25 to transition to the longitudinal component of the strut 14. The struts 14 emerge the same way at the other end, namely, extending inwardly from the tubular portion 18, curving outwardly in curved region 28, transitioning to outwardly directed angled portion 23, curving inwardly at bend 27 and transitioning to the longitudinal component of the strut 14.

The tubular portions 16, 18, containing the converging regions of the filter are spaced both axially inwardly and radially inwardly from the bend regions 25, 27 which are at the end portions of the longitudinal components of the strut.

(Axially inwardly is represented by arrow "a" and radially inwardly is represented by arrow "b") This can be appreciated by reference to FIG. 5, wherein imaginary vertical line V1 represents the two end regions of the mounting section 15, i.e. the longitudinal component of the struts, and vertical line V2 represents the end portion of the filtering sections 30, 40. V1 and V2 can also be viewed as tangent lines to the curved region of the mounting section and the curved region of the filter sections, respectively. The distalmost end point 18a of tubular portion is proximal of the distalmost end point of the mounting section and the proximalmost end point of tubular portion 16a is distal of the proximalmost end point of the mounting section.

The distances between V1 and V2 can be varied in design of the filter to alter the balance between the radial stretch of the filter and the ability to direct particles inwardly towards the center of the filter and vessel. That is, the greater the distance between V1 and V2, i.e. the greater the angle of the angled portions, the more the particles will be directed to the center of the filter and vessel. (Trapping the particles at the center rather than the edges of the filter is more desirable because there is less blood flow at the edges of the vessel and greater blood flow at the center to better dissolve the particles). However, the greater the angle (formed by the angled portion of the strut and the longitudinal axis) the less radial stretch of the filter and the decreased ability to accommodate a wide variety of vessel sizes.

The filters of the present invention are designed to optimize the balance of radial stretch to accommodate vessels of different sizes, e.g. 18 mm to 32 mm, with angled edges to direct particles toward the center of the vessel.

FIGS. 8 and 9 illustrate an alternate embodiment of the filter where the angled portions 21', 23' of the struts 14' are of a greater angle. As shown, the bends of filter 10' have a smaller radius of curvature and thus the tubular portions 16' and 18' and filtering sections are spaced less axially inwardly from the ends of the mounting section as compared to the embodiment of FIG. 5.

FIGS. 3 and 4 illustrate filter 10 in the transitional expanded configuration as it transitions from the collapsed configuration to the placement configuration. In this transitional expanded configuration, the converging ends of the filtering sections 30 and 40 are in axial alignment with the ends of the mounting section, i.e. the ends of the longitudinal struts 14. Thus, imaginary lines V1 and V2 overlap. After this initial expansion, the filter 10 returns to its expanded placement configuration wherein line V2 lies inboard of line V1 as described above and shown in FIG. 5. Also, the diameter D2 of the filter in the expanded placement configuration is greater than the diameter D1 of the collapsed (delivery) configuration, but less than the diameter D3 (FIG. 4) of the transitional expanded configuration. Therefore, in use, once deployed, the filter 10 moves from the collapsed configuration of FIG. 1 to the transitional expanded configuration of FIG. 3 and then to the expanded placement configuration of FIG. 7. In the placement (expanded) configuration, the filter 10 moves towards its memorized position and the extent it returns to its fully memorized position will be dependent on the size of the vessel in which the filter 10 is inserted. (The larger the vessel, the closer the filter comes to returning to its fully memorized position). Although in viewing FIGS. 4 and 5, it appears the length of the strut has increased, in a preferred embodiment, the strut length would remain the same as it moves from the transitional expanded configuration to the placement configuration.

To enable movement between an expanded and collapsed configuration, the filter tube of the embodiments described herein is preferably made of shape memory metal material, such as Nitinol, a nickel titanium alloy. The memorized configuration of the filter 10 is shown in FIG. 7. To facilitate passage of the filter 10 through the lumen of the delivery sheath 100 (shown in FIG. 22A in conjunction with the method of insertion) and into the vessel, cold saline is injected into the delivery sheath or catheter 100 and around the filter 10 in its collapsed position within the delivery sheath 100. This shape memory material characteristically exhibits rigidity in the austenitic state and more flexibility in the martensitic state. The cold saline maintains the temperature dependent filter 10 in a relatively softer condition as it is in the martensitic state within the sheath. This facilitates the exit of filter 10 from the sheath 100 as frictional contact between the filter 10 and the inner surface of the sheath would otherwise occur if the filter was maintained in a rigid, i.e. austenitic, condition.

Once ejected from the delivery sheath or catheter 100, the filter is no longer cooled and is exposed to the warmer body temperature, which causes the filter 10 to return towards its austenitic memorized configuration.

The filter 10 (and other filters described herein) can be inserted through the jugular vein in the neck of the patient or through the femoral vein in the leg of the patient or the arm. The filters can also be placed in the superior vena cava. Due to their symmetry, they can be positioned in either orientation. As the particles contact the filter they are directed to the center by the filtering portion, trapping them in the region of higher blood flow to improve dissolution. In either orientation of the filter when delivered, the filter portion with angled surface will direct the particles to the center as they contact the filter. Thus the use of "proximal" and "distal" herein can be reversed, depending on placement of filter.

FIGS. 22A-22C illustrate delivery and placement of the filter 10, by way of example, in the inferior vena cava. Delivery catheter 100 is inserted through the femoral vein "f" and advanced through the iliac arteries into the inferior vena cava. Delivery catheter would be withdrawn once the tip of the sheath is adjacent the structure so that withdrawal of the sheath would place the filter in the desired location of FIG. 15. Tubing 104 and valve assembly 106 enable saline injection. Delivery catheter 100 is withdrawn to enable filter 10 to be warmed by body temperature to transition to the transitional expanded configuration and subsequently the expanded placement configuration. The other filters described herein could be inserted in the same manner.

In an alternate embodiment illustrated in FIGS. 10-12, filter 110 has struts 114 which are wider, represented by reference letter w, at the elongated mounting region 119, which extends longitudinally, than at the angled portions 121 and curved regions 126. This is preferably achieved by removing material to create the thinner portions. These thinner portions increase the flexibility of the filter 110 for forming the angled portions upon deployment and the thicker portions increase the surface area contact with the vessel wall for mounting of the filter 110 within the vessel. FIGS. 10 and 11 illustrate the filter 110 in the collapsed configuration with cutouts 115 of non-uniform width cut into the tube to form the elongated struts 114. As shown, cutouts 112 are widest at the end regions 115, adjacent tubular portions 116 and 118 and thinner as they extend toward the center. This creates the widened region of struts 114 when in the expanded placement configuration of FIG. 12.

In an alternate embodiment, the filter can have elongated struts which are thinner, rather than wider as in the embodiment of FIG. 12, at the elongated mounting region, than at the angled portions and curved regions. This would provide more stability at the curved regions. In the alternate embodiment of FIG. 13, three different widths are provided. The zone 186 of filter 185 corresponding to the parallel component of the strut 184 has the greatest width, zone 188 corresponding to the angled portion of the strut 184 has a smaller width, and zone 189 corresponding to the curved region of the strut 184 has an even smaller width. The adjustment of the widths is designed to strike a balance between stability and flexibility of the various regions of the filter. Thus, other width variations are contemplated such as making zone 186 smaller in width than the zone 188 and/or zone 189, or providing a different number of width changes within each strut and/or in different struts.

In an alternate embodiment of FIGS. 18 and 19, the end portions of each of the struts are axially offset or out of phase. This offset/radial shift results in particles bypassing the first filtering portion being captured by the second filtering portion since it is out of alignment. The offset can be achieved by twisting or rotating one of the ends of the filter. In one embodiment, the ends are about 30 degrees out of phase although other variations are contemplated. Filter 50 has struts 54, preferably six in number, having a twist so that the end 57 of each strut at tubular portion 56 is out of axial alignment with its opposing end 59 at tubular portion 58. This can be understood by appreciating an imaginary line (not shown) extending from one side of a strut 54 where it extends from tubular portion 56 to the opposing side of the same strut where it extends from tubular portion 58 would be at an angle to the longitudinal axis of the filter. Thus the filtering sections would be out of alignment. In contrast, in the non-offset embodiments, such imaginary lines would be substantially parallel with the longitudinal axis of the filter. As in the embodiments described above, the filtering portions are positioned radially and axially inwardly of the end portions of the mounting sections. The struts 54 have angled or curved portions 61, 64 extending radially and axially inwardly and bends at regions 65, 68 transitioning to respective tubular portions 56, 58. For clarity, not all the struts 54 are so labeled.

In the alternate embodiment of FIG. 21A, connecting ribs 192 connect the struts 194 of filter 190. This increases the stability of the filter 190. As shown, the two ribs 192 extend from adjacent struts 194 and are joined at region 196. The ribs 192 curve inwardly as shown. The ribs 192 can be arranged so they are axially aligned as in FIG. 21B or can be spaced axially as shown in the embodiment of FIG. 21C where ribs 197 between elongated struts 198 of filter 195 are axially displaced. The ribs can be placed between fewer than all the struts and the ribs can be utilized with any of the foregoing embodiments. Note that the ribs are shown attached to the struts, however, preferably the ribs would be integrally formed with the filter, formed by the laser cutting process mentioned above.

In another embodiment, the ribs could curve radially outward near their tips, thus contacting the vessel wall and acting as a retaining mechanism.

FIGS. 20A and 20B illustrate another alternate embodiment of the vessel filter having a converging intermediate region. Filter 80 is similar to filter 10 except that instead of mounting sections extending longitudinally and substantially parallel to the vessel wall, the end regions of the struts 89 form the mounting sections as the struts 84 converge into tubular portion 81 at an intermediate or central portion of filter 80. Stated another away, filter 80 has a first mounting section 82 and a first filtering section 83 positioned between central tubular portion 81 and tubular portion 85 and a second mounting section 89 and second filtering section 86 positioned between central tubular portion 81 and tubular portion 87. Barbs, roughened surfaces or other anchoring elements can be formed on the outer surface of curved regions 88 of struts 84 to enhance engagement with the vessel wall. Note that like the earlier versions, the filtering portions 83, 86 are inboard (radially and axially inward) of the mounting sections 82, 89. The struts 84 are preferably formed from a single tubular member with cutouts 91. The ends of the strut 84 can alternately be axially offset as in the embodiments of FIGS. 18 and 19 and the struts can have varying width.

The foregoing filters can be inserted through the femoral vein of alternatively through the internal jugular vein. It can also be removed from either direction, e.g. from access through the inferior vena cava or through the internal jugular vein. Various methods can be used to remove the filter such as those described in commonly assigned co-pending application Ser. No. 09/911,097, filed Jul. 23, 2001 and published Dec. 19, 2002 as publication no. US 2002-0193827A1, the entire contents of which is incorporated herein by reference, including for example, slotted hooks, graspers, etc. A recess or cutout can also be provided at the tubular end portions to receive a snare or other device for removal. Such recess is illustrated in the embodiment of FIGS. 14A-14C and designated by reference numeral 70.

To facilitate removal of the filter from the vessel, cold saline can be injected onto the implanted filter to change the temperature of the filter to move it to a relatively softer condition to facilitate the filter being drawn in to the retrieval sheath. That is, injection of cold saline will cause the filter to approach its martensitic state, bringing the filter to a more flexible condition. The flexible condition facilitates the collapse and withdrawal of the filter into the retrieval sheath, by decreasing the frictional contact between the filter and the inner surface of the retrieval sheath.

While the above description contains many specifics, those specifics should not be construed as limitations on the scope of the disclosure, but merely as exemplifications of preferred embodiments thereof. For example, the filters can be inserted in other regions of the body. Also, any of the aforedescribed filters can have mounting sections of varying thickness. The foregoing filters can be made of materials other than shape memory material. Those skilled in the art will envision many other possible variations that are within the scope and spirit of the disclosure as defined by the claims appended hereto.

What is claimed is:

1. A vessel filter comprising a tubular member having a distal portion and a proximal portion, a longitudinal axis and a plurality of elongated cutouts formed therein extending along the longitudinal axis and forming a series of elongated spaced apart struts separated by the cutouts, the filter movable between a first insertion configuration and a second deployed configuration, each of the spaced apart struts in the deployed configuration forming longitudinally extending linear struts extending substantially parallel to the longitudinal axis of the filter to form a mounting section and each including a first inwardly bent region at a first end bending towards a center of the filter to transition to a first filter section and a second inwardly bent region at a second end bending towards a center of the filter to transition to a second filter section, the first inwardly bent region transitioning into a linear strut region, the linear strut region transitioning into a first curved region curving away from the center of the filter, and the second inwardly bent region transitioning into a linear strut region, the linear strut region transitioning into a second curved region curving away from the center of the filter, the first curved region extending into an inner portion of a first tubular portion and the second curved region extending into an inner portion of a second tubular portion, the inner portion of the first and second tubular portions being the portions closer to the center of the filter, the first bent region positioned distal of the first tubular portion and the second bent region positioned proximal of the second tubular portion such that a first imaginary line tangent to the first bent region of the struts and perpendicular to the longitudinal axis does not intersect the first tubular portion and a second imaginary line tangent to the second bent region of the struts and perpendicular to the longitudinal axis region does not intersect the second tubular portion such that the first imaginary line is distal of the first tubular portion and the second imaginary line is proximal of the second tubular portion.

2. The vessel filter of claim 1, wherein the longitudinal struts include roughened surfaces to engage the vessel wall to increase retention.

3. The vessel filter of claim 1, further comprising a plurality of vessel engaging members with pointed ends extending from the longitudinally extending struts to engage the vessel wall to increase retention.

4. The vessel filter of claim 1, wherein the filter is composed of shape memory material.

5. The vessel filter of claim 1, wherein opposing ends of at least one of the longitudinally extending struts are out of phase.

6. The vessel filter of claim 1, wherein the longitudinally extending struts are spaced circumferentially about 60 degrees apart.

7. The vessel filter of claim 1, wherein at least one of the struts has varying widths along its length, the strut having an angled portion, a portion of the strut substantially parallel to the longitudinal axis of the filter having a first width and the angled portion of the strut having a second width less than the first width.

8. The vessel filter of claim 1, wherein the longitudinally extending struts include a plurality of vessel engaging members extending therefrom to engage the vessel wall to increase retention.

9. The vessel filter of claim 1, wherein end portions of at least one of the longitudinally extending struts are twisted out of phase.

10. The vessel filter of claim 1, wherein the struts have a length exceeding a diameter of the filter.

11. The vessel filter of claim 1, further comprising curved ribs extending from adjacent struts.

12. The vessel filter of claim 11, wherein the curved ribs terminate in a joined region.

13. The vessel filter of claim 1, wherein the struts at the first filter section originate from an inner end of the first tubular portion and at the second filter section originate from an inner end of the second tubular portion.

* * * * *